United States Patent [19]

Burke et al.

[11] Patent Number: 5,484,446
[45] Date of Patent: Jan. 16, 1996

[54] ALIGNMENT GUIDE FOR USE IN ORTHOPAEDIC SURGERY

[75] Inventors: Dennis W. Burke, Milton, Mass.; Thomas Petersen, San Diego, Calif.; David Krueger, Warsaw; Rodney L. Bays, Pierceton, both of Ind.

[73] Assignee: Zimmer, Inc., Warsaw, Ind.

[21] Appl. No.: 265,884

[22] Filed: Jun. 27, 1994

[51] Int. Cl.⁶ .......................... A61B 17/15; A61B 17/17
[52] U.S. Cl. ................... 606/87; 606/86; 606/96
[58] Field of Search ................... 606/86, 87, 88, 606/89, 96, 98

[56] References Cited

U.S. PATENT DOCUMENTS

| | | | |
|---|---|---|---|
| 4,421,112 | 12/1983 | Mains et al. | |
| 4,567,885 | 2/1986 | Androphy | |
| 4,703,751 | 11/1970 | Pohl | 606/87 |
| 4,738,254 | 4/1988 | Buechel et al. | |
| 4,759,350 | 7/1988 | Dunn et al. | |
| 4,791,919 | 12/1988 | Elloy et al. | |
| 4,892,093 | 1/1990 | Zarnowski et al. | 606/82 |
| 4,952,213 | 8/1990 | Bowman et al. | 606/79 |
| 5,053,037 | 10/1991 | Lackey | 606/88 |
| 5,098,383 | 3/1992 | Hemmy et al. | 604/116 |
| 5,122,144 | 6/1992 | Bert et al. | 606/88 |
| 5,234,433 | 8/1993 | Bert et al. | 606/88 |
| 5,250,050 | 10/1993 | Poggie et al. | 606/79 |

FOREIGN PATENT DOCUMENTS

| | | |
|---|---|---|
| 0104732 | 4/1984 | European Pat. Off. |
| 0380451 | 8/1990 | European Pat. Off. |

Primary Examiner—Stephen C. Pellegrino
Assistant Examiner—Scott B. Markow
Attorney, Agent, or Firm—Todd A. Dawson

[57] ABSTRACT

The alignment guide of this invention includes a cam rotatable about the longitudinal axis of the alignment guide as defined by an intramedullary rod. A base plate is pivotally connected to the intramedullary rod and includes a pair of cam followers positioned on opposite sides of the intramedullary rod. In use, as the cam is rotated relative to the rod, the cam followers ride against the cam causing the plate to pivot or angulate relative to the rod. A plurality of indicia are formed on the cam to indicate to the surgeon the relative angle between the plate and the rod. The base plate includes a quick connect mechanism to permit the surgeon to quickly attach a device such as a cutting guide or pinning guide to the base plate. The cutting guide is fixed relative to the base plate such that the cutting guide will be at the same angular orientation as the plate relative to the intramedullary rod.

7 Claims, 4 Drawing Sheets

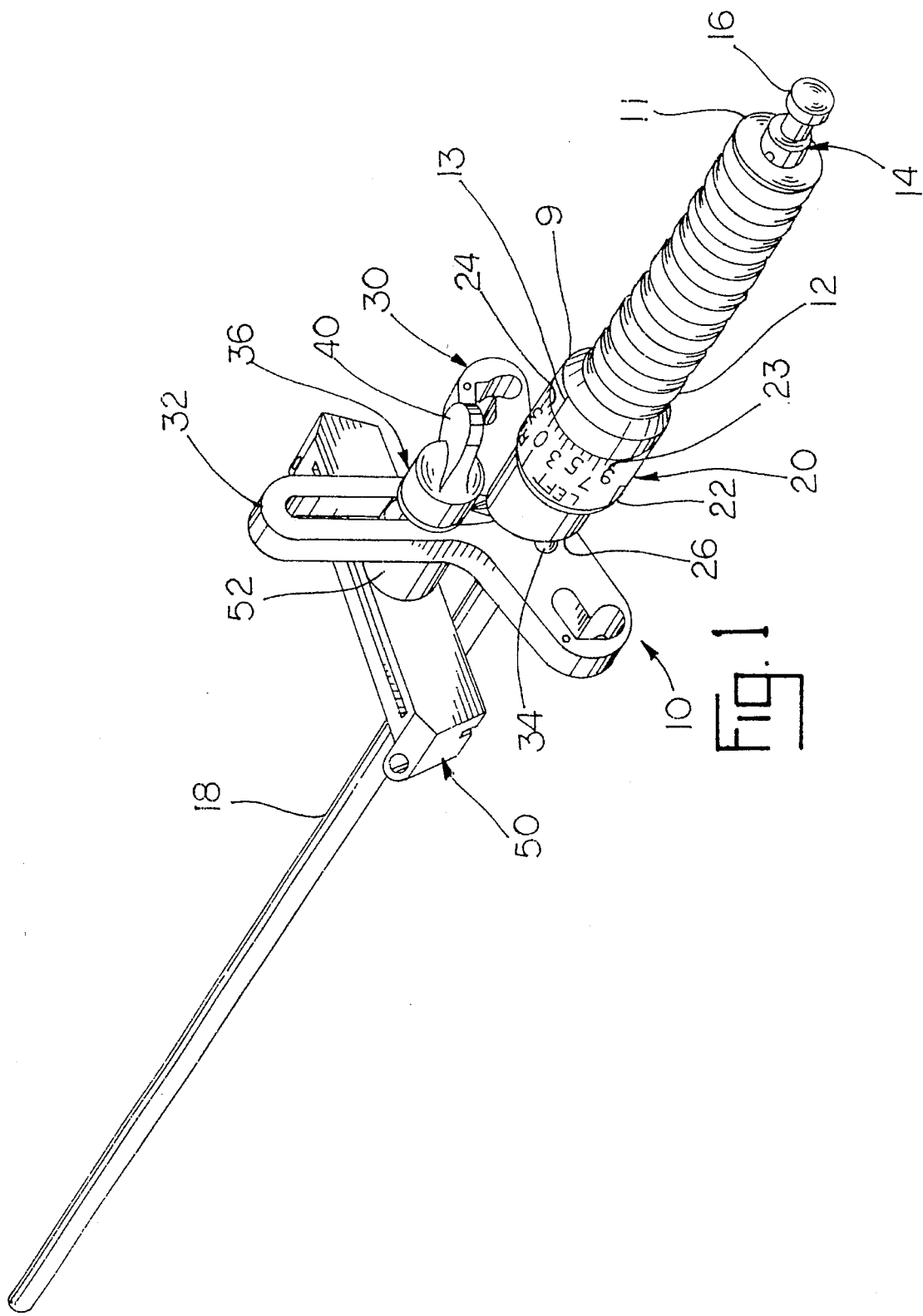

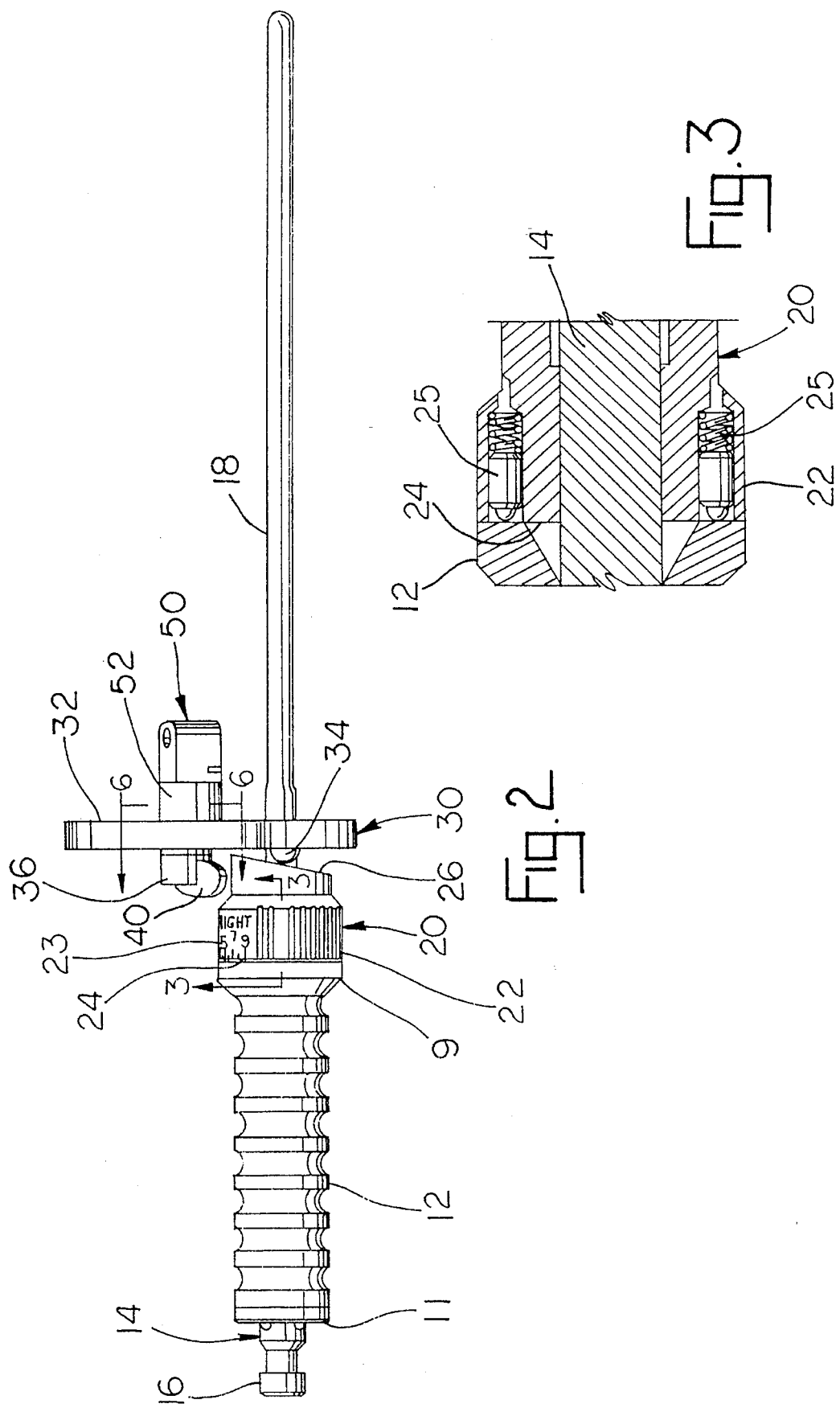

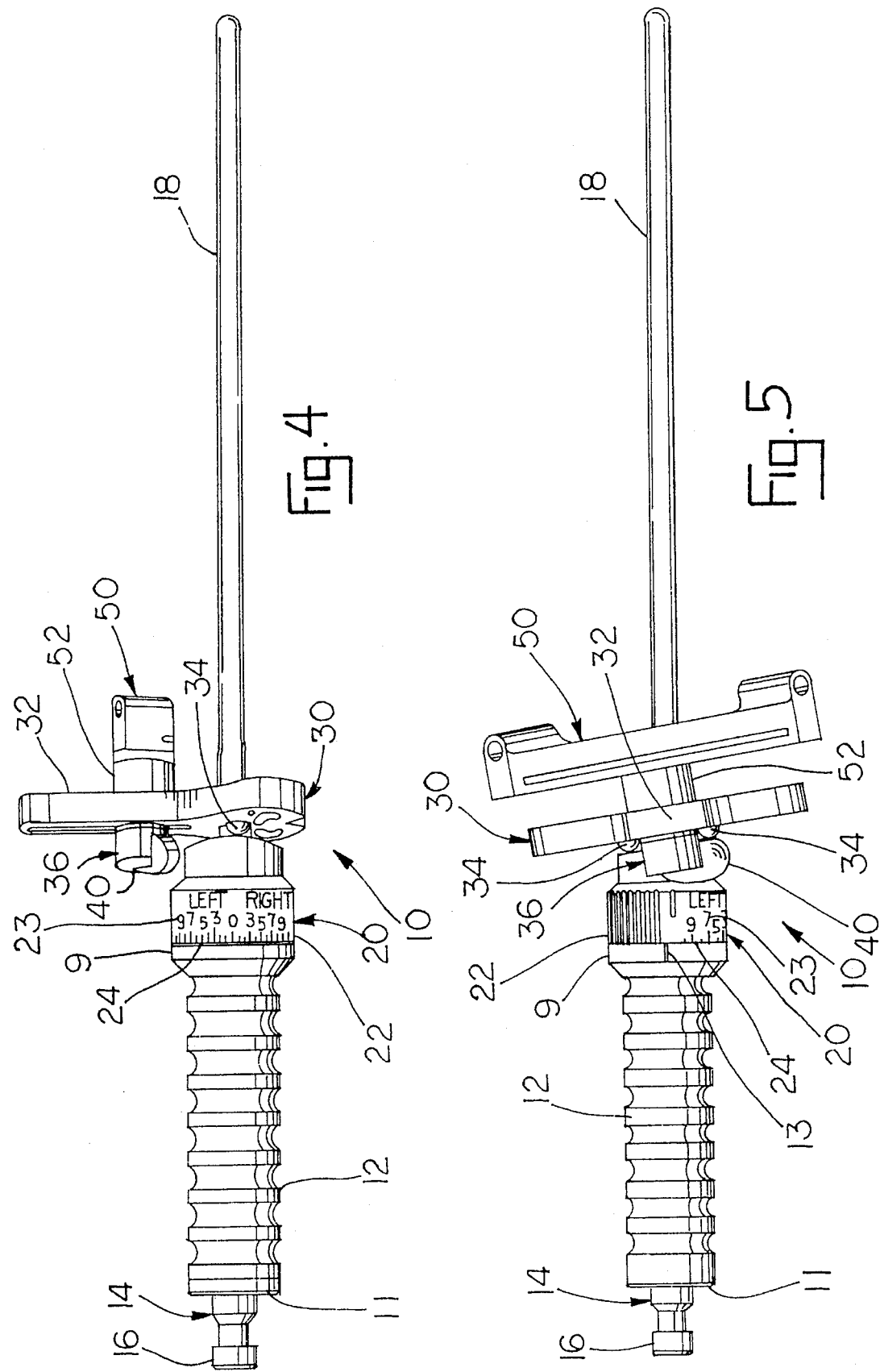

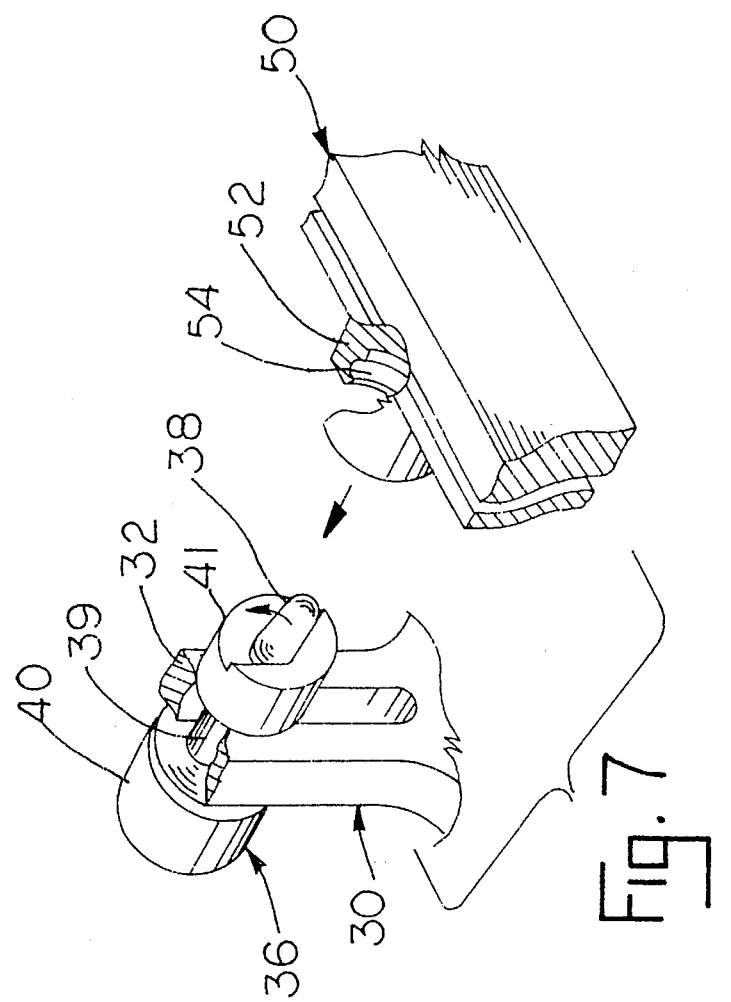
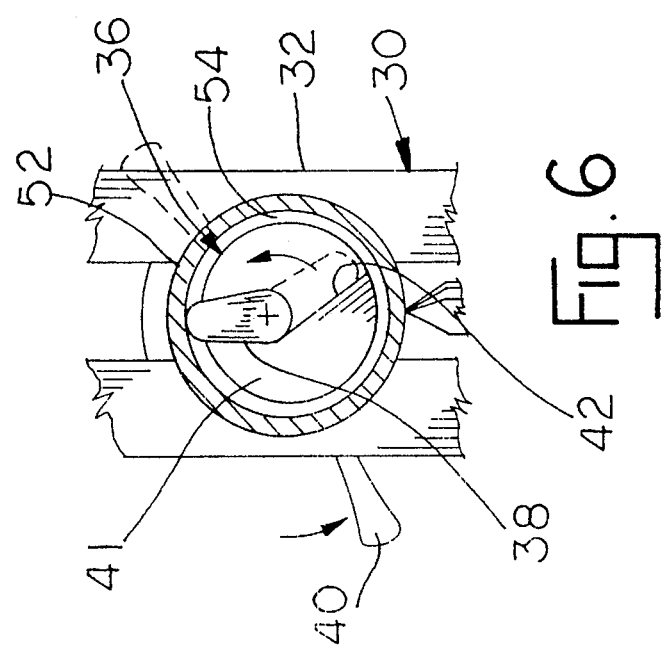

5,484,446

ALIGNMENT GUIDE FOR USE IN ORTHOPAEDIC SURGERY

FIELD OF THE INVENTION

This invention relates to orthopaedic instruments and has specific relevance to an intramedullary alignment guide having a rotatable cam means to provide angular adjustment between the intramedullary rod and a reference plate carried by the guide.

BACKGROUND OF THE INVENTION

In joint replacement surgery the surgeon may be required to make several cuts through the bone to prepare the patient's bones for the prosthetic knee implant. Over the years, a multitude of instruments have been developed to assist the surgeon in accurately aligning the various cuts with reference to the anatomical axes of the patient's joint. Many of these devices are adjustable to permit the surgeon to position the instrument at an appropriate angle.

SUMMARY OF THE INVENTION

The alignment guide of this invention includes a cam rotatable about the longitudinal axis of the alignment guide as defined by an intramedullary rod. A base plate is pivotally connected to the intramedullary rod and includes a pair of cam followers positioned on opposite sides of the intramedullary rod. In use, as the cam is rotated relative to the rod, the cam followers ride against the cam causing the plate to pivot or angulate relative to the rod. A plurality of indicia are formed on the cam to indicate to the surgeon the relative angle between the plate and the rod. The base plate includes a quick connect mechanism to permit the surgeon to quickly attach a device such as a cutting guide or pinning guide to the base plate. The cutting guide is fixed relative to the base plate such that the cutting guide will be at the same angular orientation as the plate relative to the intramedullary rod.

Accordingly, it is an object of the invention to provide for a novel alignment guide for orthopaedic surgery.

Another object of the invention is to provide for a novel adjustment mechanism for an alignment guide for use in orthopaedic surgery.

Still another object of the invention is to provide for a novel locking mechanism for attaching a cutting head to an alignment guide.

Still other objects of the invention will become apparent upon a reading of the following description taken with the accompanying drawings.

BRIEF DESCRIPTION OF THE DRAWINGS

FIG. 1 is a perspective view of the alignment guide of this invention.

FIG. 2 is a side elevational view of the alignment guide of the invention.

FIG. 3 is a sectional view taken along lines 3—3 of FIG. 2.

FIG. 4 a side elevational view of the alignment guide of the invention with the cam fully rotated.

FIG. 5 is a top elevational view of FIG. 4.

FIG. 6 is a sectional view taken along lines 6—6 of FIG. 2.

FIG. 7 is an enlarged view of the quick connect mechanism with portions sectioned for illustrative purposes.

DESCRIPTION OF THE PREFERRED EMBODIMENT

The preferred embodiment herein described is not intended to be exhaustive or to limit the invention to the precise form disclosed. Rather, it is chosen and described to best explain the invention so that others skilled in the art might utilize its teachings.

Referring now to the drawings, alignment guide 10 includes a handle 12 which includes a plurality of annular grooves to provide a roughened surface for gripping by the surgeon. Handle 12 includes a central longitudinal bore which accommodates a portion of intramedullary rod 14. Rod 14 is secured relative to the handle by a pin or screw (not shown) or other suitable means. A small portion 16 of rod 14 extends outwardly of end 11 handle 12 and forms a means for attaching a known extracting instrument to the guide. A larger portion 18 of rod 14 extends from end 9 of handle 12 and is configured to extend into an intramedullary canal of a bone during a joint replacement surgery.

A cam 20 is carried by rod 14 adjacent handle end 9 and is rotatable about the rod relative to handle 12. Cam 20 includes a generally cylindrical body 22 having a first end 24 which is generally perpendicular to the periphery of body 22. End 24 is positioned adjacent end 9 of handle 12. Cam 20 includes a second end 26 which is positioned at an angle as illustrated relative to the end 24 of body 22. Cam 20 is therefore generally wedge shaped with the second end 26 forming the caming surface for cam 20. A plurality of indicia 23 are formed on body 22 and when aligned with a notch 13 of handle 12 provides an indication to the surgeon of the relative angle between rod 18 and base plate 30. A pair of spring biased plungers 25 (see FIG. 3) are carried within blind bores formed in cam body 22 and engage small detents (not shown) within handle 12 on a mating surface of end 9 to provide a series of positive stop positions for the cam relative to the handle as the cam is rotated.

A base plate 30, shaped as illustrated, is connected to intramedullary rod 14 by a pin (not shown) and is pivotal about the pin relative to rod 14. A pair of protrusions or cam followers 34 extend from plate 30 toward cam 20 and contact the second surface 26 of the cam. Cam followers 34 are positioned on opposite sides of rod 14. Plate 30 may include openings for accommodating other instruments such as spacer buttons or plates for offsetting the alignment guide from the bone. A tower 32 extends from base plate 30 and is co-planer with the plate. Tower 32 includes a longitudinal slot as shown. A coupling device 36 is shiftably carried by tower 32 and is positioned within the slot.

Coupling device 36 (illustrated best in FIG. 7) includes a generally ovoid latch 38 having a rod 39 coupled to one end thereof. A finger actuated knob 40 is connected to the opposite end of rod 39. Rod 39 extends through the slot in tower 32 and through base 41. Base 41 as illustrated includes a generally V-shaped recessed area 42 which accommodates latch 38 and defines its rotational limits. Rod 39 passes through base 41 off center such that the tip of latch 38 extends beyond the side periphery of base 41 when the latch is rotated into the position of FIG. 6. When latch 38 is rotated by rod 39 into the position shown in phantom lines in FIG. 6, the tip of the latch lays interior to the side periphery of the base. Coupling device 36 further includes a compression spring (not shown) extending between knob 40 and base 41 to frictionally hold the coupling device to the tower.

The cutting guide 50 includes a body having a slot therethrough for accommodating a surgical saw blade.

Guide 50 further includes a hollow cylindrical protrusion 52 which includes an annular grove 54 formed therein. In use, guide 50 is connected to tower 32 by coupling device 36. Cylindrical protrusion 52 is placed over base 40 and latch 38 is rotated into the position illustrated in FIG. 6 wherein the tip of the latch extends beyond the side periphery of the base and into annular grove 54 of the protrusion. To unlock the guide 50, latch 38 is rotated by rod 39 so as to be positioned as shown in phantom lines in FIG. 6 out of annular groove 54. Guide 50 may be slid off of coupling device 36.

To angulate base 30 relative to rod 18, the surgeon rotates cam 20 relative to the rod. Cam followers 34 in contact with camming surface 26 of cam 20 cause base 30 to rotate about its pivot pin (not shown) to position the plate at an angle relative to the rod. The indicia provided on the cam indicates the relative angle to the surgeon. It should be understood that the cutting device 50, or any other device, connected to the plate will also be positioned at the same angle relative to the rod.

It should also be understood that although a cutting guide is illustrated, any number of instruments could be attached to the plate using the coupling mechanism so the device includes a cylinder with an internal groove as described above.

Finally, it should be understood that the invention is not to be limited to specific details above but may be altered within the scope of the appended claims.

We claim:

1. An alignment guide for an orthopaedic instrument, the alignment guide including an intramedullary rod, a base plate pivotally connected adjacent one end of the rod, and a cam means carried by the rod in engagement with cam follower mounted on the base plate for orienting the base plate at an angle relative to the rod.

2. The alignment guide of claim 1 wherein the cam means includes a generally cylindrical cam rotationally positioned about the rod, the cam including a camming face, the plate having at least one cam follower in contact with the camming face.

3. The alignment guide of claim 2 wherein the cylindrical cam includes a central through bore for accommodating a portion of the rod and lies in a plane generally transverse to the rod.

4. The alignment guide of claim 1 further including indicia on an exterior periphery of the cam means for indicating the relative angle between the rod and the base plate.

5. The alignment guide of claim 1 further including a coupling means carried by the base plate for connecting a device to the base plate, said coupling means including a latch mechanism which is positionable in a first position, wherein a portion of the latch mechanism is configured to extend into the device and a second position wherein the portion of the latch mechanism is configured to be spaced from the device.

6. The alignment guide of claim 5 wherein the coupling means is positioned eccentric to the base plate such that in the first position one end of the coupling means extends beyond a periphery of the base plate and in a second position the one end of the coupling means is positioned interior of the periphery of the base plate.

7. A resection guide for use in orthopaedic surgery to guide a cutting device for resection of a portion of a patient's bone to accommodate an orthopaedic implant, the resection guide including an intramedullary rod configured for insertion into an intramedullary canal of a patient's bone, a base pivotally connected to the rod and lying in a plane generally transverse to the rod, a cam carried by the rod and rotatable relative thereto, the base having at least one cam follower in engagement with the cam, wherein as the cam is rotated about the rod the relative angle between the rod and the base is varied, and a cutting guide connected to the base for guiding a resection instrument.

\* \* \* \* \*